US012797024B2

(12) United States Patent
Pyeon et al.

(10) Patent No.: US 12,797,024 B2
(45) Date of Patent: Nov. 17, 2026

(54) MAMMOGRAPHY APPARATUS AND DRIVE METHOD THEREOF

(71) Applicant: Vieworks Co., Ltd., Anyang-si (KR)

(72) Inventors: Yeong Hyeon Pyeon, Anyang-si (KR); Junho Oh, Seoul (KR)

(73) Assignee: Vieworks Co., Ltd., Anyang-si (KR)

( * ) Notice: Subject to any disclaimer, the term of this patent is extended or adjusted under 35 U.S.C. 154(b) by 142 days.

(21) Appl. No.: 19/035,009

(22) Filed: Jan. 23, 2025

(65) Prior Publication Data

US 2025/0235173 A1 Jul. 24, 2025

(30) Foreign Application Priority Data

Jan. 23, 2024 (KR) ........................ 10-2024-0010454

(51) Int. Cl.
*A61B 6/50* (2024.01)
*A61B 6/04* (2006.01)

(52) U.S. Cl.
CPC ............ *A61B 6/502* (2013.01); *A61B 6/0414* (2013.01); *A61B 6/0435* (2013.01)

(58) Field of Classification Search
CPC ..... A61B 6/502; A61B 6/0414; A61B 6/0435; A61B 6/54; A61B 2562/0252
See application file for complete search history.

(56) References Cited

U.S. PATENT DOCUMENTS 5,506,877 A * 4/1996 Niklason ................ A61B 6/502 378/208
5,851,180 A * 12/1998 Crosby ................ A61B 6/0414 600/407
6,577,703 B2 6/2003 Krister et al.
9,782,135 B2 10/2017 Stango et al.
10,603,002 B2 3/2020 Stango et al.
2014/0016741 A1* 1/2014 Mertelmeier ........ A61B 6/0414 378/37
2016/0183889 A1* 6/2016 Matsuura ............. A61B 6/0414 378/37
2020/0359974 A1 11/2020 Defreitas et al.

FOREIGN PATENT DOCUMENTS

JP H0386154 A * 4/1991
JP 5355619 B2 11/2013
JP 2017-225634 A 12/2017
KR 10-2017-0060291 A 6/2017

OTHER PUBLICATIONS

Strubel Christine, "European Search Report for EP Application No. 25153360.0", May 30, 2025, EPO, Germany.
Strubel Christine, "European Search Report for EP Application No. 25153360.0", May 30, 2024, EPO, Germany.

* cited by examiner

*Primary Examiner* — Kiho Kim
(74) *Attorney, Agent, or Firm* — Bridgeway IP Law Group, PLLC; Jihun Kim

(57) ABSTRACT

Embodiments relate to a mammography apparatus and a method of operating the same, and more particularly, to a mammography apparatus and a method of operating the same, the mammography apparatus being capable of positioning an object at an exact position in case that the object is pressed so that an image of the object is captured by the mammography apparatus, and minimizing pain caused by a load applied to the object.

14 Claims, 7 Drawing Sheets

MAMMOGRAPHY APPARATUS AND DRIVE METHOD THEREOF

CROSS-REFERENCE TO RELATED APPLICATIONS

This application claims priority to and the benefit of Korean Patent Application No. 10-2024-0010454 filed in the Korean Intellectual Property Office on Jan. 23, 2024, the entire contents of which are incorporated herein by reference.

TECHNICAL FIELD

The present invention relates to a mammography apparatus and a method of operating the same, and more particularly, to a mammography apparatus and a method of operating the same, the mammography apparatus being capable of positioning an object at an exact position in case that the object is pressed so that an image of the object is captured by the mammography apparatus, and minimizing pain caused by a load applied to the object.

BACKGROUND ART

Recently, an incidence rate of breast cancer in women has been gradually increased because of westernized dietary habits. Therefore, it is necessary for women to be periodically diagnosed and managed.

Methods of diagnosing breast cancer include breast ultrasonography and breast magnetic resonance imaging (MRI), but a mammography apparatus using X-rays is representatively used.

The mammography apparatus acquires X-ray images of breasts from an image receptor after exposure to an appropriate dose of X-rays through an automatic exposure control (AEC) device.

The mammography apparatus in the related art includes an emission part configured to emit X-rays, an imaging part provided to face the emission part, and a compression paddle configured to rectilinearly reciprocate between the emission part and the imaging part.

FIG. 7 illustrates operations of a compression paddle 50 and an imaging part 40 in the mammography apparatus in the related art.

As illustrated in FIG. 7, the above-mentioned compression paddle 50 is raised or lowered by a drive part and presses a measurement object, e.g., a breast A of a woman with a predetermined load.

In this case, the breast A placed on the imaging part 40 has a curved shape. For this reason, when the compression paddle 50 presses the breast A while being merely raised or lowered, a shape of the breast A may be distorted, or a load may be concentrated on a part of a surface of the breast A, which may cause severe pain to the patient.

In addition, as illustrated in FIG. 7, in order to prevent the distortion of the shape of the breast or the withdrawal of the breast when the breast A is pressed, the user fixes the patient's breast A with one hand H and then presses the breast A while applying a force to the breast A from inside to outside. In this case, because the user's hand H is positioned between the compression paddle 50 and the breast A, which causes an inconvenience in adjusting a position of the hand. Further, one hand needs to be used, which makes it difficult to set the patient's posture.

SUMMARY OF THE INVENTION

The present invention has been made in an effort to solve the above-mentioned problem, and an object of the present invention is to provide a mammography apparatus capable of preventing a breast shape from being distorted or a load from being concentrated on a part of a breast surface in case that an image of an object, such as a woman's breast, is captured.

The present invention has also been made in an effort to provide a mammography apparatus capable of ensuring a space in which a user's hand may fix an object in case that the object is pressed by a compression paddle, and implementing an operation of the user's hand smoothing the object downward from inside to outside in case that the object is pressed by the compression paddle.

The objects of the present invention may be achieved by a mammography apparatus including: a main body part; an emission part provided on a front surface of the main body part and configured to emit radioactive rays toward an object; an imaging part provided on the front surface of the main body part and configured to face the emission part; and a compression part provided on the front surface of the main body part and disposed between the emission part and the imaging part, the compression part being provided on the front surface of the main body part and configured to be raised or lowered, moved forward or rearward, and rotated to press the object.

In this case, the compression part may include: a load cell provided on the front surface of the main body part, configured to be raised or lowered, and configured to measure a load applied to the object by the compression part; a movement frame connected to the load cell, configured to be movable relative to the load cell, and configured to be moved forward or rearward relative to the load cell; and a compression paddle provided to be rotatable relative to the movement frame and configured to press the object.

In addition, the movement frame may include: a rotary hinge to which the compression paddle is rotatably connected; and a rotational drive part configured to rotate the compression paddle about the rotary hinge.

In the embodiment, the movement frame may further include a paddle fixing part rotatably connected to the rotary hinge and connected to the compression paddle.

In addition, the movement frame may further include: a drive pin configured to rotate the paddle fixing part about the rotary hinge by being rectilinearly moved by the rotational drive part; and an elastic member provided on the rotary hinge and configured to apply an elastic force in a direction opposite to a direction in which the drive pin pushes the paddle fixing part.

In the embodiment, the mammography apparatus according to the present invention may further include: an arm part to which the emission part and the imaging part are coupled to face each other, the arm part being coupled to the front surface of the main body part, in which the load cell is coupled to a sliding plate slidably coupled to the arm part.

In addition, one end of the load cell may be fixed to a fixing bracket coupled to the sliding plate and forms a fixed end.

In addition, the present invention provides a method of operating a mammography apparatus, which includes a load cell provided on a front surface of a main body part, configured to be raised or lowered, and configured to measure a load applied to an object, and a compression paddle configured to be moved forward or rearward and rotated relative to the load cell and configured to press the object, the method including: a first pressing step of pressing the object by the compression paddle by lowering the load cell until a first load is reached; and a second pressing step of pressing the object by the compression paddle by additionally lowering the load cell until a second load is reached.

In the embodiment, in the first pressing step, the object may be pressed by the compression paddle in a state in which the compression paddle is moved forward by a predetermined distance in a direction toward the object and the compression paddle is rotated in a first rotation direction toward the object.

In addition, in the second pressing step, the object may be pressed by the compression paddle in a state in which the compression paddle is rotated in a second rotation direction away from the object.

Furthermore, in the second pressing step, the object may be pressed by the compression paddle in a state in which the compression paddle is moved rearward by a predetermined distance in a direction away from the object.

In the embodiment, an imaging part may be further provided on the front surface of the main body part, and in the second pressing step, an end of the compression paddle may be disposed on a vertical line identical to an end of the imaging part.

In the embodiment, the method of operating the mammography apparatus may further include: an additional pressing step of pressing the object with the second load or higher.

In this case, an imaging part may be further provided on the front surface of the main body part, and in the additional pressing step, the load cell may be lowered, and an end of the compression paddle may be disposed on a vertical line identical to an end of the imaging part.

In addition, in the additional pressing step, the compression paddle may rotate in the other rotation direction away from the object when a measured elastic modulus of the object is a predetermined reference value or more.

According to the present invention configured as described above, it is possible to reduce the patient's pain by preventing the breast shape from being distorted or a load from being concentrated on a part of the breast surface in case that an image of the object, such as a woman's breast, is captured.

In addition, according to the present invention, it is possible to more efficiently perform the imaging process by ensuring the space in which the user's hand may fix the object in case that the object is pressed by a compression paddle, and implementing the operation of the user's hand smoothing the object downward from inside to outside in case that the object is pressed by the compression paddle.

The foregoing summary is illustrative only and is not intended to be in any way limiting. In addition to the illustrative aspects, embodiments, and features described above, further aspects, embodiments, and features will become apparent by reference to the drawings and the following detailed description.

Figure 1:
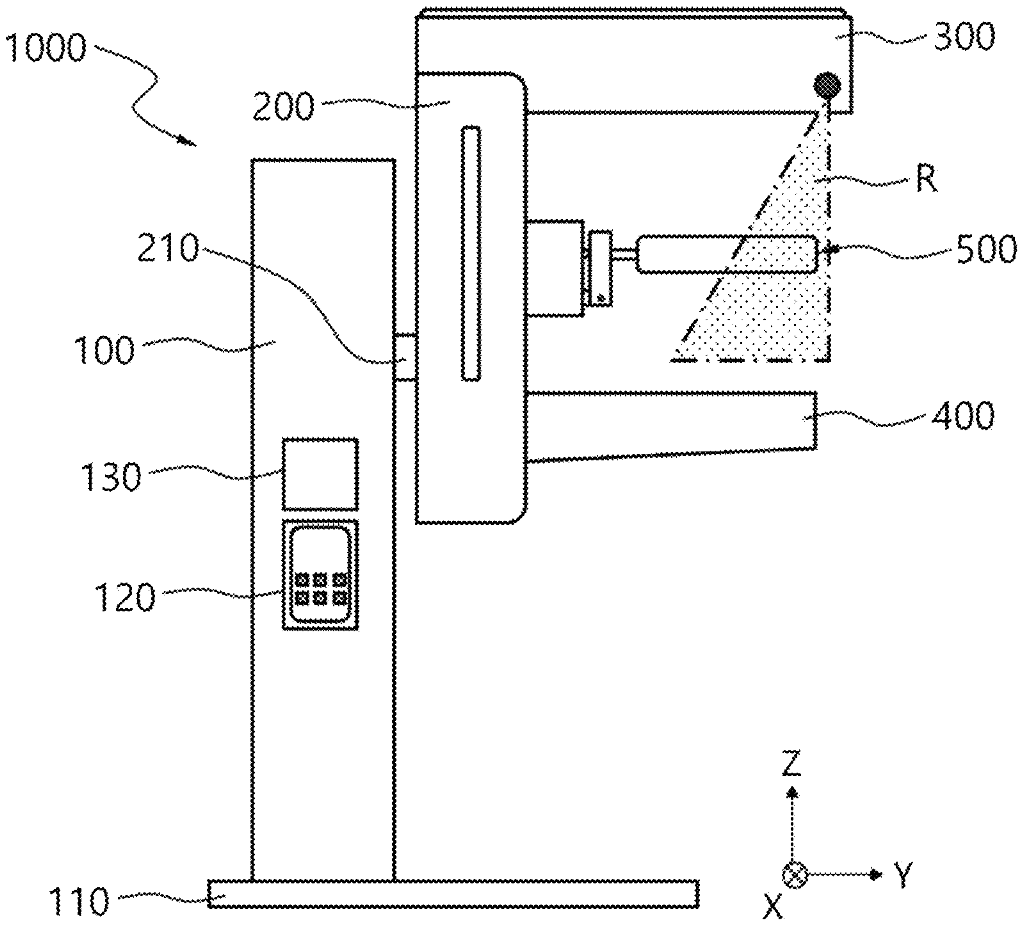
FIG. 1 is a side view of a mammography apparatus according to an embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, a mammography apparatus and a method of operating the same according to an embodiment of the present invention will be described in detail with reference to the drawings.

FIG. 1 is a side view of a mammography apparatus 1000 according to an embodiment of the present invention.

Figure 4:
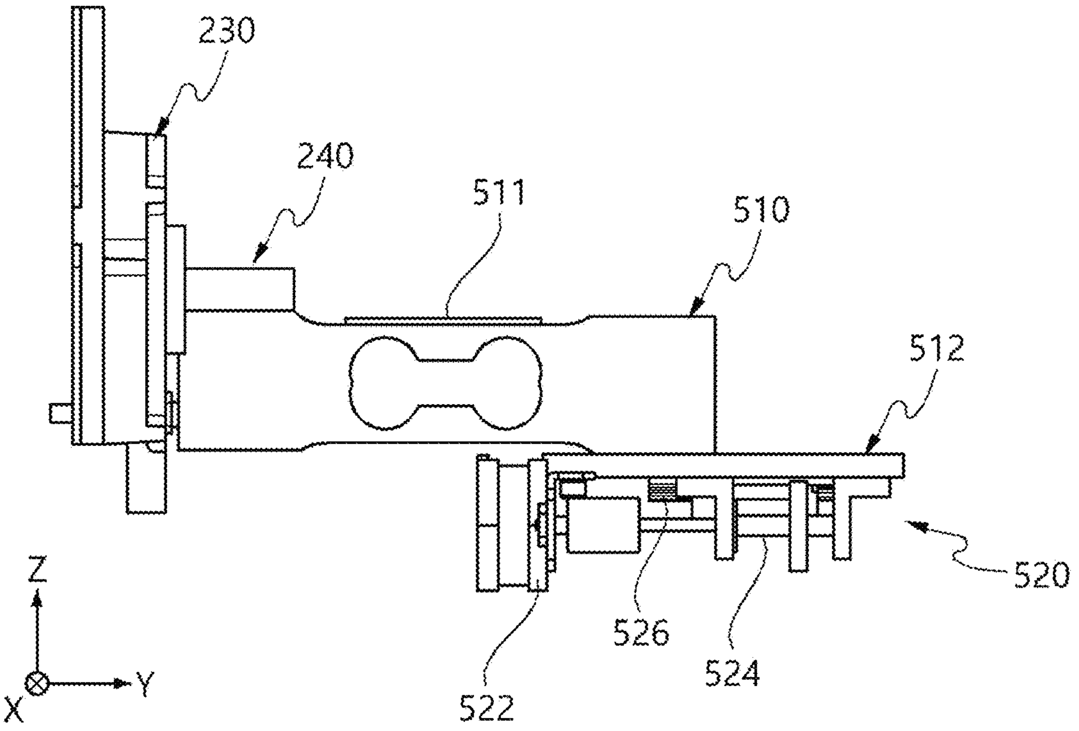
FIG. 4 is a side view illustrating one embodiment of the load cell, a connection plate, and a horizontal movement part in the mammography apparatus according to the embodiment of the present invention.

With reference to FIG. 1, the mammography apparatus 1000 includes a main body part 100, and a compression part 500 configured to press an object A (see FIG. 4). In the embodiment, the compression part 500 may be raised or lowered in a Z-axis direction along a front surface of the main body part 100, moved forward or rearward in a Y-axis direction, and rotated about an X-axis.

The main body part 100 may be installed by being connected to a base 110 installed on a ground surface or a floor. The main body part 100 may be provided with a controller (not illustrated) configured to control an operation of the mammography apparatus 1000.

In addition, a manipulation part 120 may be provided at one side of the main body part 100 so that a user may input an instruction or the like. A display 130 may be provided at one side of the main body part 100 to display various types of states of the mammography apparatus 1000.

An arm part 200 may be connected to the front surface of the main body part 100 and configured to be rotatable about a rotary shaft 210.

Meanwhile, an emission part 300 configured to emit radioactive rays toward the object may be provided on the front surface of the main body part 100. An imaging part 400 may be provided on the front surface of the main body part 100 and face the emission part 300.

Specifically, the emission part 300 and the imaging part 400 may be provided on the arm part 200. The emission part 300 and the imaging part 400 may be disposed on the arm part 200 and face each other.

The emission part 300 emits radioactive rays R, such as X-rays, toward the object A, and the imaging part 400 may capture an image of the object A.

The apparatus in the related art has a structure in which the compression part 500 is merely raised or lowered. Because the woman's breast, which is the object, has a curved shape, the breast shape may be distorted or a load is concentrated on a part of the breast surface when the breast is merely pressed parallelly by the compression part, which may cause severe pain to the patient.

In addition, in order to prevent the distortion of the shape of the breast or the withdrawal of the breast when the breast is pressed, the user fixes the patient's breast with one hand and then presses the breast while applying a force to the breast from inside to outside. In this case, because the user's hand is positioned between the compression part and the breast, which causes an inconvenience in adjusting a position of the hand. Further, one hand needs to be used, which makes it difficult to adjust the patient's posture.

In the present invention, in order to solve the above-mentioned problem, the compression part 500 may be raised or lowered in the Z-axis direction along the front surface of the main body part 100, moved forward or rearward in the Y-axis direction, and/or rotated about the X-axis. In the embodiment, the compression part 500 may be provided on the arm part 200 and disposed between the emission part 300 and the imaging part 400.

In this case, the compression part 500 may be raised or lowered in the vertical direction (or the Z-axis direction) along the arm part 200. The compression part 500 may be moved on the arm part 200 forward toward the object A (or in the Y-axis direction) so as to become close to the object A or moved rearward away from the object A. Further, the compression part 500 may be rotatably provided on the arm part 200. In this case, the compression part 500 may rotate about the X-axis. In case that the object A is seated on the imaging part 400, the compression part 500 may rotate in one rotation direction (clockwise based on FIG. 1) toward the object A or rotate in the other rotation direction (counterclockwise based on FIG. 1) away from the object A.

Figure 2:
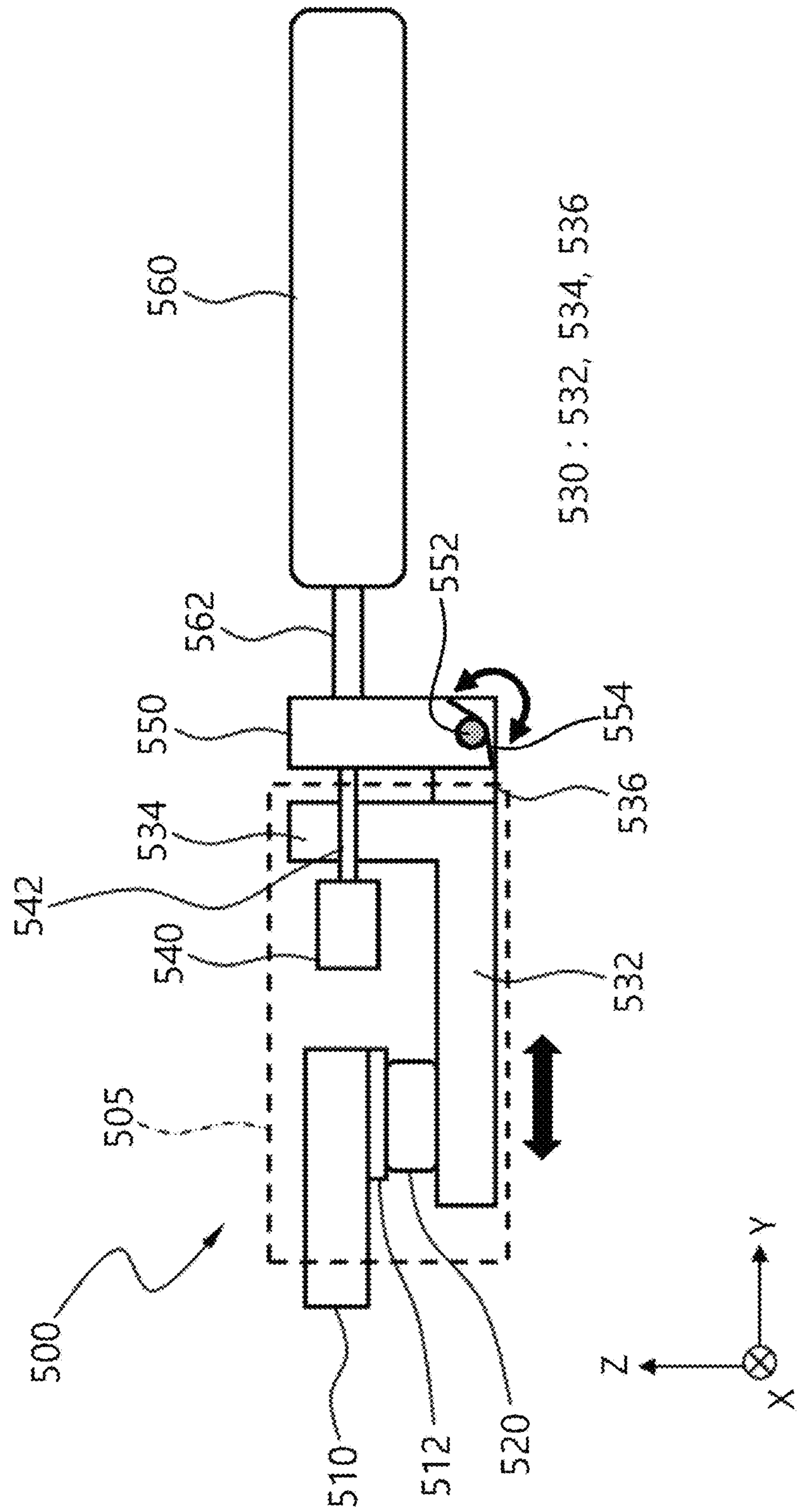
FIG. 2 is a side view illustrating a compression part of the mammography apparatus according to the embodiment of the present invention.

FIG. 2 is a side view illustrating the compression part 500 of the mammography apparatus according to the embodiment of the present invention.

With reference to FIGS. 1 and 2, the compression part 500 may include a load cell 510 configured to measure a load applied to the object A by the compression part 500, a movement frame 530 connected to the load cell 510, configured to be movable relative to the load cell 510, and configured to be moved forward or rearward relative to the load cell 510, and a compression paddle 560 configured to be rotatable relative to the movement frame 530 and configured to press the object A.

The load cell 510 may be provided on the front surface of the main body part 100 and configured to be raised or lowered. More specifically, the load cell 510 may be provided on the arm part 200 and configured to be raised or lowered. For example, the load cell 510 may be raised or lowered by a rectilinear motion mechanism such as a linear motion (LM) drive part or a rack/pinion mechanism provided on the arm part 200 in the vertical direction. The configuration for raising or lowering the load cell 510 in the vertical direction may be variously modified without being specifically limited.

The load cell 510 measures a load applied to the object A by the compression paddle 560. The measured load may be transmitted to the above-mentioned controller and utilized as data by the controller configured to control the operation of the mammography apparatus 1000.

Meanwhile, the movement frame 530 may be connected to the load cell 510 and configured to be movable relative to the movement frame 530. FIG. 2 illustrates a case in which the movement frame 530 is configured to move forward toward the object A (or in the Y-axis direction) relative to the load cell 510 so as to become close to the object A or move rearward away from the object A.

However, the present invention is not limited thereto. A configuration may be implemented in which the load cell 510 is movable forward or rearward or both the load cell 510 and the movement frame 530 are movable forward or rearward. Hereinafter, the configuration in which the movement frame 530 is connected to the load cell 510 and configured to be movable forward or rearward will be described.

The movement frame 530 may be connected to the load cell 510 by means of a horizontal movement part 520. For example, a connection plate 512 may be connected to the load cell 510, and the horizontal movement part 520 may be connected to the connection plate 512. For example, the horizontal movement part 520 may be configured as a linear motion (LM) drive part. In this case, an LM guide, a motor, a ball screw, and the like, which constitute the linear motion (LM) drive part, may be installed on the connection plate 512. The configuration of the horizontal movement part 520 may be variously modified without being specifically limited.

Meanwhile, the movement frame 530 may be connected to be moved forward toward the object A (or in the Y-axis direction) or moved rearward by the horizontal movement part 520.

Specifically, the movement frame 530 may include a rotary hinge 552 to which the compression paddle 560 is rotatably connected, and a rotational drive part 540 configured to rotate the compression paddle 560 about the rotary hinge 552.

For example, the movement frame 530 may include a horizontal frame 532 connected to the horizontal movement part 520, and a vertical frame 534 vertically bent from the horizontal frame 532. The horizontal frame 532 may be movably connected to the horizontal movement part 520.

In addition, the rotary hinge 552 may be provided at one side of the horizontal frame 532. The rotary hinge 552 may be installed on the horizontal frame 532. Alternatively, as illustrated in FIG. 2, the rotary hinge 552 may be installed on an extension frame 536 extending from one side of the horizontal frame 532.

In the embodiment, a paddle fixing part 550 may be rotatably connected to the rotary hinge 552. The paddle fixing part 550 may be connected to the compression paddle 560 by means of a connection bar 562 and configured to be rotatable about the rotary hinge 552.

Meanwhile, the rotational drive part 540 may be connected to the vertical frame 534. The rotational drive part 540 may be connected to the vertical frame 534 by means of a connection rib (not illustrated) or the like.

In addition, the rotational drive part 540 may be connected to a drive pin 542. The drive pin 542 serves to rotate the paddle fixing part 550 about the rotary hinge 552 while being rectilinearly moved by the rotational drive part 540. In this case, the drive pin 542 may be disposed while penetrating the vertical frame 534.

Therefore, when the drive pin 542 pushes the paddle fixing part 550 toward the object A (or in the Y-axis direction) by the operation of the rotational drive part 540, the paddle fixing part 550 and the compression paddle 560 are rotated about the rotary hinge 552 in one rotation direction (or clockwise) toward the object A.

Meanwhile, an elastic member 554 may be provided on the rotary hinge 552 and apply an elastic force in a direction opposite to the direction in which the drive pin 542 pushes the paddle fixing part 550 or the compression paddle 560. For example, the elastic member may be configured as a torsion spring or the like.

Therefore, in case that the compression paddle 560 is intended to be rotated in a first rotation direction (clockwise in FIG. 2), the drive pin 542 pushes the paddle fixing part 550 toward the object A (or in the Y-axis direction) by the operation of the rotational drive part 540.

In addition, in case that the compression paddle 560 is intended to be rotated in a second rotation direction (counterclockwise in FIG. 2, i.e., the direction away from the object), the drive pin 542 is moved rearward by the operation of the rotational drive part 540 in the direction away from the object A, and the paddle fixing part 550 and the compression paddle 560 are rotated in the second rotation direction by the elastic member 554.

Meanwhile, the compression part 500 may have a housing 505, and the above-mentioned constituent elements may be disposed in the housing 505.

For example, the movement frame 530, the rotational drive part 540, and the horizontal movement part 520 may be provided inside the housing 505. In addition, the load cell 510 may protrude from a rear end of the housing 505 and be connected to the arm part 200. Further, the paddle fixing part 550 may be rotatably disposed at a front end of the housing 505, and the compression paddle 560 may be connected to the front surface of the paddle fixing part 550.

Figure 3:
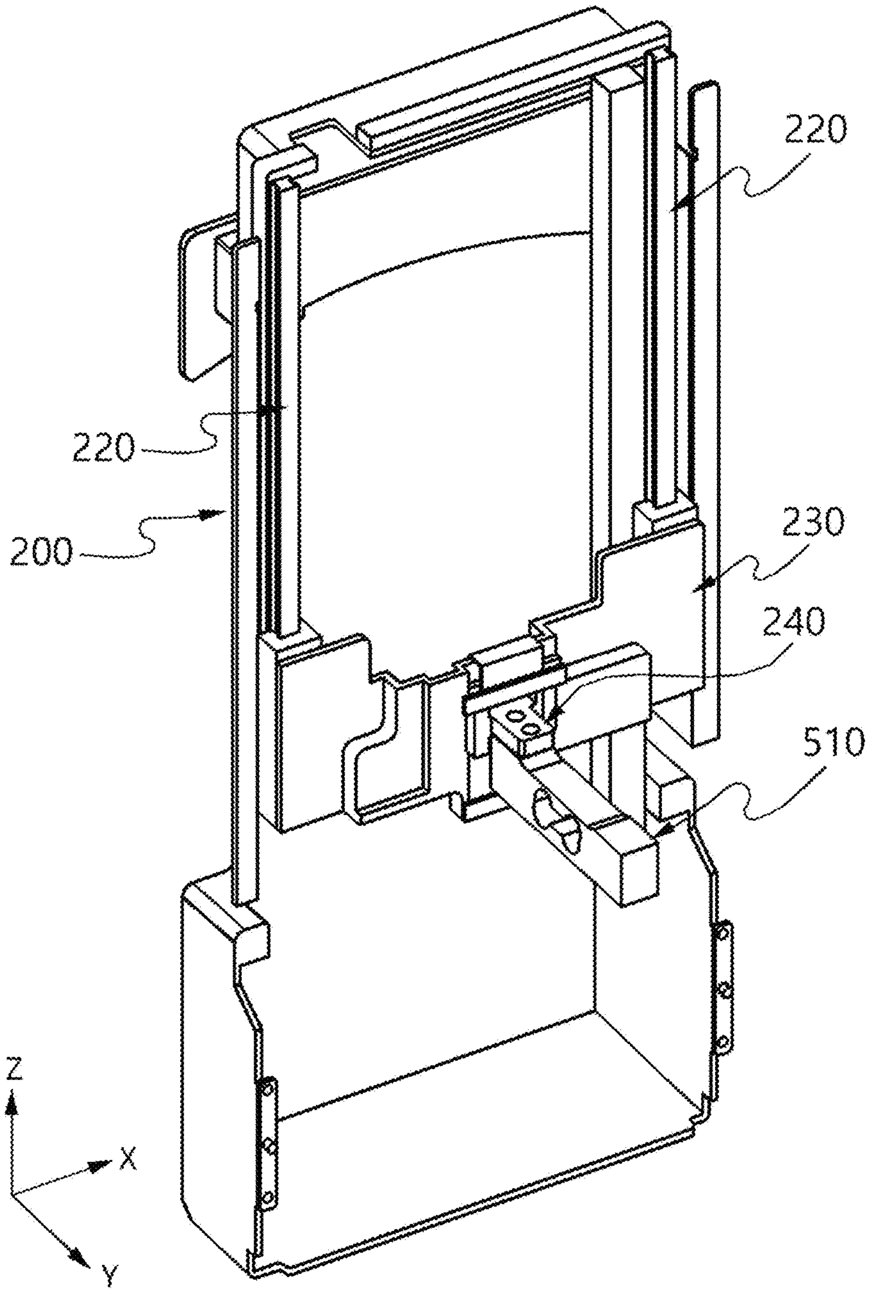
FIG. 3 is a view illustrating a state in which a load cell is mounted on an arm part by means of a mounting plate in the mammography apparatus according to the embodiment of the present invention.

FIG. 3 is a view illustrating a state in which the load cell is mounted on the arm part by means of a mounting plate in the mammography apparatus according to the embodiment of the present invention, and FIG. 4 is a side view illustrating one embodiment of the load cell, the connection plate, and the horizontal movement part in the mammography apparatus according to the embodiment of the present invention.

With reference to FIGS. 3 and 4, one end of the load cell 510 is fixed to a sliding plate 230, such that the load cell 510 may be provided on the arm part 200 and configured to be slidable in an upward/downward direction (Z-axis direction). In the embodiment, the sliding plate 230 may move upward or downward along sliding rails 220 provided on one side surface of the arm part 200. The sliding plate 230 is operated upward or downward by a rectilinear motion mechanism such as the LM drive part or the rack/pinion mechanism described above, such that the load cell 510 may move in the upward/downward direction. One end of the load cell 510 may be fixed to a fixing bracket 240 fixed to the sliding plate 230.

With reference to FIG. 4, one end of the load cell 510 is fixed to the fixing bracket 240 and forms a fixed end, and the other end of the load cell 510 forms a free end at which the connection plate 512 is provided. The load cell 510 may have a strain gauge 511, and the strain gauge 511 may sense a load transmitted through the connection plate 512 and applied to the compression paddle 560. The horizontal movement part 520 is provided on a bottom surface of the connection plate 512. In the embodiment, the horizontal movement part 520 includes an LM guide 526, a motor 522, and a ball screw 524.

As described above, the horizontal movement part 520 may move the movement frame 530 in the Y-axis direction.

In the present invention, the load cell 510 may be understood as serving as a support bar for supporting the horizontal movement part 520, the movement frame 530, and the compression paddle 560 while serving to measure a load applied to the compression paddle 560.

Figure 5:
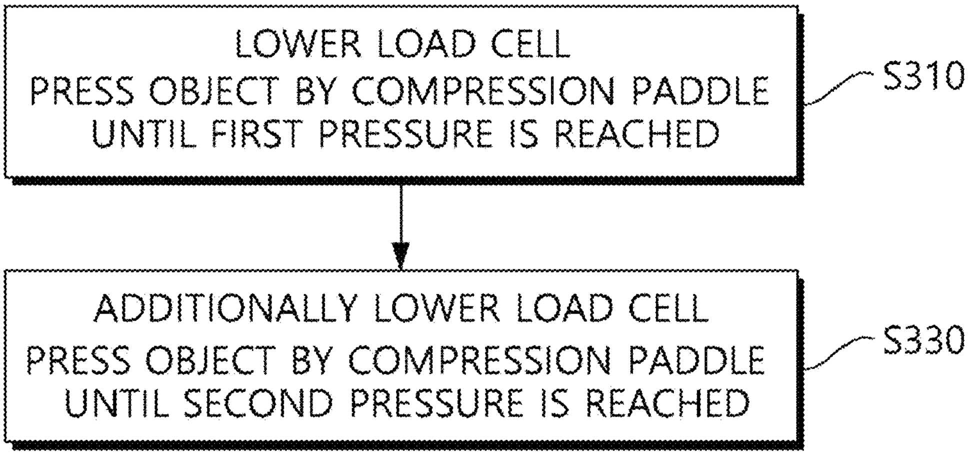
FIG. 5 is a flowchart illustrating a method of operating the mammography apparatus according to the embodiment of the present invention.
Figure 6:
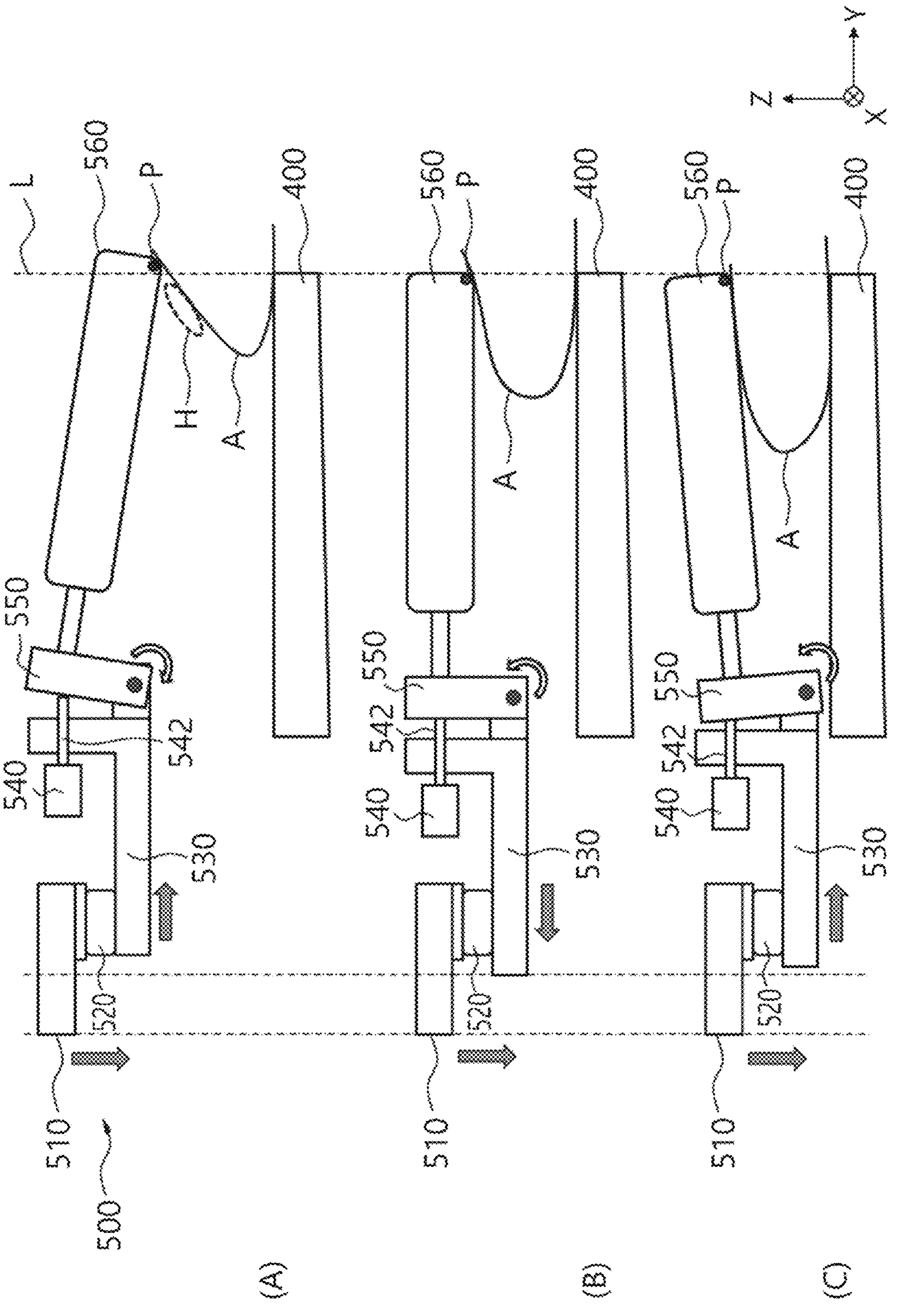
FIG. 6 is a view illustrating an operation of the compression part of the mammography apparatus according to the embodiment of the present invention.
Figure 7:
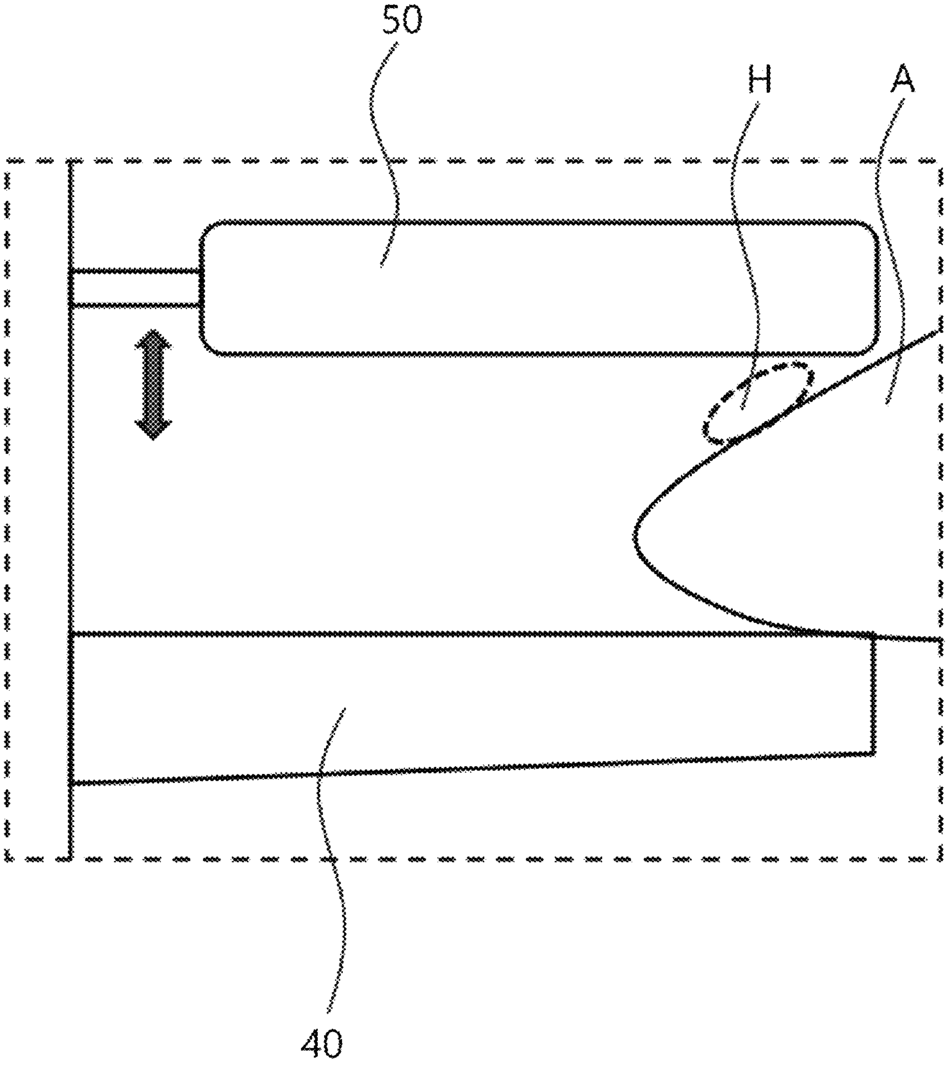
FIG. 7 is a view schematically illustrating an operation of a mammography apparatus in the related art.

Hereinafter, an operation method, which presses the object A by using the mammography apparatus 1000 configured as described above, will be described. FIG. 5 is a flowchart illustrating a method of operating the mammography apparatus 1000 according to the embodiment of the present invention, and FIG. 6 is a view illustrating an operation of the compression part of the mammography apparatus 1000 according to the embodiment of the present invention. FIG. 4 illustrates only the compression part 500, the imaging part 400, and the object A.

With reference to FIGS. 5 and 6, the operation method may include a first pressing step S310 of pressing, by the compression paddle 560, the object A by lowering the load cell 510 until a first load is reached, and a second pressing step S330 of pressing, by the compression paddle 560, the object A by additionally lowering the load cell 510 until a second load is reached.

Further, the operation method may further include a preparation step prior to the first pressing step S310.

In the preparation step, the compression part 500 is moved to a location above the object A. In the embodiment, the horizontal movement part 520 moves the movement frame 530 forward in the Y-axis direction in a state in which the load cell 510 is positioned to be higher in height than the object A, such that the compression paddle 560 may be positioned above the object A.

Next, as illustrated in FIG. 6A, the first pressing step may be performed. In the first pressing step, the load cell 510 is lowered.

Specifically, in case that the load cell 510 is lowered, the movement frame 530 and the compression paddle 560 are also lowered in conjunction with the load cell 510.

In this case, the paddle fixing part 550 is pushed toward the object A by the drive pin 542 of the rotational drive part 540, such that the compression paddle 560 may be rotated about the rotary hinge 552 by a predetermined rotation angle in the first rotation direction (clockwise in FIG. 6 or in the direction toward the object).

When the compression paddle 560 rotates in one rotation direction toward the object A, a compression point P on a lower portion of a leading end portion of the compression paddle 560 adjoins and presses the object A.

In the embodiment, an end of the compression paddle 560, i.e., the compression point P may be adjusted to protrude by a predetermined distance from a vertical line L identical to an end of the imaging part 400. Therefore, when the load cell 510 and the compression paddle 560 are lowered, an inner side of the object A may be pressed first by the compression point P, as illustrated in FIG. 6A.

In the above-mentioned first pressing step, as illustrated in FIG. 6A, a space is formed between a lower portion of the compression paddle 560 and the object A, such that a practitioner may put their hand H into the space and adjust a posture of the object A.

The first pressing step may be performed until the load measured by the load cell 510 reaches the first load. That is, the load cell 510 is continuously lowered until the load measured by the load cell 510 reaches the first load.

In this case, the first load may be appropriately selected. For example, the first load may be set to about 10 N. However, the first load may be appropriately adjusted in consideration of a patient's body type, body weight, height, age, and the like. The first load is not specifically limited.

Meanwhile, when the load measured by the load cell 510 reaches the first load, the second pressing step may be performed, as illustrated in FIG. 4B.

The second pressing step may be performed by additionally lowering the load cell 510 until the load measured by the load cell 510 reaches the second load.

In the embodiment, the horizontal movement part 520 moves the movement frame 530 rearward while the load cell 510 is lowered in the second pressing step, such that the compression paddle 560 may be moved by a predetermined distance in the direction away from the object A, and the compression paddle 560 may be rotated by the rotational drive part 540 in the second rotation direction away from the object A (counterclockwise in FIG. 6).

The compression paddle 560 rotates in the second rotation direction until the compression paddle 560 maintains the horizontality. The compression paddle 560 is lowered until the second load is reached.

In the second pressing step, the operation of the compression paddle 560 is similar to an operation of the user smoothing the object A downward, such that it is possible to minimize pain that the patient may feel because of a load applied to the object A.

In the second pressing step, the load cell 510 and the compression paddle 560 are lowered until the load measured by the load cell 510, which presses the object A, reaches the second load. The second load may be appropriately selected. For example, the second load may be set to about 50 N. However, the second load may be appropriately adjusted in consideration of the patient's body type, body weight, height, age, and the like. The second load is not specifically limited.

In addition, as the compression paddle 560 moves rearward, the end of the compression paddle 560 or the compression point P may be disposed on the vertical line L identical to the end of the imaging part 400.

When the load measured by the load cell 510 reaches the second load, the second pressing step is ended, and the downward movement of the load cell 510 is stopped.

Meanwhile, subsequent to the above-mentioned second pressing step, an additional pressing step of pressing the object A with the second load or higher may be performed depending on the user's selection.

For example, the user may input an instruction by using the manipulation part 120 in order to perform the additional pressing step.

As illustrated in FIG. 6C, in the additional pressing step, the load cell 510 is lowered additionally and presses the object A in the state in which the compression paddle 560 maintains the horizontality. In this case, the end of the compression paddle 560, i.e., the compression point P may be disposed on the vertical line L identical to the end of the imaging part 400.

In this case, an elastic modulus of the object A may be measured by calculating the amount of increase in load measured by the load cell 510. When the elastic modulus, which is measured as described above, is a predetermined reference value or more, a gradient of the compression paddle 560 may be adjusted or the compression paddle 560 may be rotated so that the compression point P is kept disposed on the vertical line L identical to the end of the imaging part 400.

For example, the compression paddle 560 may rotate in the second rotation direction away from the object A (counterclockwise in FIG. 6) so that the compression point P is disposed on the vertical line L identical to the end of the imaging part 400.

Therefore, the compression paddle 560 has a shape in which the end of the compression paddle 560 is lifted toward the object A. In case that the load cell 510 is lowered, the object A may be uniformly pressed by a lower end of the compression paddle 560.

In addition, the compression paddle 560 may move forward in the direction toward the object A so that the compression point P is disposed on the vertical line L identical to the end of the imaging part 400.

While the present invention has been described above with reference to the exemplary embodiments in the present application, the present invention may be variously modified and changed by those skilled in the art without departing from the spirit and scope of the present invention disclosed in the claims. Accordingly, when the modified embodiments basically include the components of the claims of the present invention, it should be considered that the modified embodiments belong to the technical scope of the present invention.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A mammography apparatus, comprising:
- a main body part;
- an emission part disposed on a front surface of the main body part and configured to emit radioactive rays toward an object;
- an imaging part disposed on the front surface of the main body part and configured to face the emission part; and
- a compression part disposed on the front surface of the main body part and disposed between the emission part and the imaging part, the compression part being configured to be raised or lowered, moved forward or rearward, and rotated to press the object,
- wherein the compression part comprises:
- a load cell disposed on the front surface of the main body part, configured to be raised or lowered, and configured to measure a load applied to the object by the compression part;
- a movement frame connected to the load cell, configured to be movable relative to the load cell, and configured to be moved forward or rearward relative to the load cell; and
- a compression paddle disposed to be rotatable relative to the movement frame and configured to press the object.

2. The mammography apparatus of claim 1, wherein the movement frame comprises:
- a rotary hinge to which the compression paddle is rotatably connected; and
- a rotational drive part configured to rotate the compression paddle about the rotary hinge.

3. The mammography apparatus of claim 2, wherein the movement frame further comprises a paddle fixing part rotatably connected to the rotary hinge and connected to the compression paddle.

4. The mammography apparatus of claim 3, wherein the movement frame further comprises:

a drive pin configured to rotate the paddle fixing part about the rotary hinge by being linearly moved by the rotational drive part; and an elastic member disposed on the rotary hinge and configured to apply an elastic force in a direction opposite to a direction in which the drive pin pushes the paddle fixing part.

5. The mammography apparatus of claim 1, further comprising:

an arm part to which the emission part and the imaging part are coupled to face each other, the arm part being coupled to the front surface of the main body part, wherein the load cell is coupled to a sliding plate slidably coupled to the arm part.

6. The mammography apparatus of claim 5, wherein one end of the load cell is fixed to a fixing bracket coupled to the sliding plate and defines a fixed end.

7. A method of operating a mammography apparatus, which comprises a load cell provided on a front surface of a main body part, configured to be raised or lowered, and configured to measure a load applied to an object, and a compression paddle configured to be moved forward or rearward and rotated relative to the load cell and configured to press the object, the method comprising:

a first pressing step of pressing the object by the compression paddle by lowering the load cell until a first load is reached; and a second pressing step of pressing the object by the compression paddle by additionally lowering the load cell until a second load is reached.

8. The method of claim 7, wherein in the first pressing step, the object is pressed by the compression paddle in a state in which the compression paddle is moved forward by a predetermined distance in a direction toward the object and the compression paddle is rotated in a first rotation direction toward the object.

9. The method of claim 7, wherein in the second pressing step, the object is pressed by the compression paddle in a state in which the compression paddle is rotated in a second rotation direction away from the object.

10. The method of claim 9, wherein in the second pressing step, the object is pressed by the compression paddle in a state in which the compression paddle is moved rearward by a predetermined distance in a direction away from the object.

11. The method of claim 9, wherein an imaging part is further disposed on the front surface of the main body part, and wherein in the second pressing step, an end of the compression paddle is disposed on a vertical line identical to an end of the imaging part.

12. The method of claim 7, further comprising:

an additional pressing step of pressing the object with the second load or higher.

13. The method of claim 12, wherein an imaging part is further disposed on the front surface of the main body part, and wherein in the additional pressing step, the load cell is lowered, and an end of the compression paddle is disposed on a vertical line identical to an end of the imaging part.

14. The method of claim 13, wherein in the additional pressing step, the compression paddle rotates in another rotation direction away from the object when a measured elastic modulus of the object is a predetermined reference value or more.

* * * * *